United States Patent [19]

Wright et al.

[11] Patent Number: 4,729,996

[45] Date of Patent: Mar. 8, 1988

[54] ANTITUMOR COMPOSITIONS AND THEIR METHODS OF USE

[75] Inventors: Amy E. Wright, Ft. Pierce; Winnie C. Thompson, Vero Beach, both of Fla.

[73] Assignee: Harbor Branch Oceanographic Institution, Inc., Ft. Pierce, Fla.

[21] Appl. No.: 868,795

[22] Filed: May 29, 1986

[51] Int. Cl.$^4$ .................. C07D 521/00; A61K 31/55
[52] U.S. Cl. ...................................... 514/215; 540/521
[58] Field of Search ....................... 540/521; 514/215

[56] References Cited

PUBLICATIONS

Nanteuil et al., "Tetrahedron", vol. 41, No. 24, pp. 6019–6033 (1985).

Primary Examiner—Robert T. Bond
Attorney, Agent, or Firm—Carroll F. Palmer

[57] ABSTRACT

This invention relates to antitumor compositions and derivatives thereof, a process of producing the compositions and a method for inhibiting tumors utilizing the compositions. More particularly, the compositions are derived from marine organisms, i.e., marine sponges *Teichaxinella morchella* and *Ptilocaulis walperis*.

20 Claims, No Drawings

ANTITUMOR COMPOSITIONS AND THEIR METHODS OF USE

FIELD OF THE INVENTION

This invention relates to new cyclic organic compounds which have useful antitumor activity. More particularly, this invention relates to new derivative antitumor compositions derived from marine sponges, i.e., *Teichaxinella morchella* and *Ptilocaulis walpersi*.

BACKGROUND OF THE INVENTION

Various tumor related diseases inflict man. Considerable research has been devoted to oncology and antitumor measures. Tumors are common in a variety of mammals and the prevention, control of the growth and regression of tumors in mammals is important to man. The term tumor refers to abnormal masses of new tissue growth which is discordant with the economy of the tissue of origin or of the host's body as a whole.

Tumors inflict mammals and man with a variety of disorders and conditions including various forms of cancer and resultant cancerous cachexia. Cancerous cachexia refers to the symptomatic discomfort that accompanies the infliction of a mammal with a tumor. These symptoms include weakened condition of the inflicted mammal as evidenced by, for example, weight loss. The seriousness of cancer is well known, e.g., cancer is second only to heart and vascular diseases as a cause of death in man.

Considerable research and resources have been devoted to oncology and antitumor measures including chemotherapy. While certain methods and chemical compositions have been developed which aid in inhibiting, remitting or controlling the growth of tumors new methods and antitumor chemical compositions are needed.

It has now been found that certain organic compounds derived from extracts of marine sponges *Teichaxinella morchella* and *Ptilocaulis walpersi* possess useful antitumor activity.

SUMMARY OF THE INVENTION

It is therefore an object of the invention to provide novel compositions which are useful as antitumor agents and a process for producing such novel antitumor compositions.

Additional objects and advantages of the invention will be set forth, in part, in the description which follows and in part will be obvious from this description, or may be learned by the practice of the invention. The objects and advantages of the invention are realized and obtained by means of the compositions, processes, methods, and the combinations particularly pointed out in the appended claims.

To achieve the objects in accordance with the purposes of the invention, as embodied and fully described here, the invention comprises compositions of the general formula I:

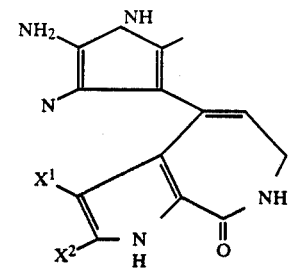

wherein $X^1$ and $X^2$ are the same or different and are a halogen, or hydrogen with the proviso that $X^1$ and $X^2$ are not both bromine.

The invention also comprises compositions which are acid salts of the compositions according to formula I, which will be referred to hereinafter as "acid salt derivatives".

In preferred embodiments of the invention, the composition is substantially pure and $X^1$ or $X^2$ is bromine or hydrogen.

As embodied and fully described herein, the invention also comprises an antitumor composition comprising, as active ingredient, an effective antitumor amount of one or more compositions according to formula I or their acid salt derivatives and a non-toxic pharmaceutically acceptable carrier or diluent.

As embodied and fully described herein, the invention also comprises a process to produce the compositions of formula I and their acid salt derivatives. The process comprises the steps of collecting marine sponges *Teichaxinella morchella* and *Ptilocaulis walpersi*; contacting the sponges with a suitable organic solvent; obtaining a solvent mixture extract thereof; and isolating a composition according to formula I from the extract.

In preferred embodiments of the invention the suitable organic solvent is selected from the group consisting of methanol, toluene, acetone, water, ethanol, n-butanol and mixtures thereof.

As embodied and fully described herein, the invention further comprises a method for inhibiting tumors in a host and a therapeutic method for treating cancerous cachexia comprising contacting a tumor with an effective antitumor amount of one or more compositions of formula I and their acid salt derivatives.

It is to be understood that both the foregoing general and the following detailed description are exemplary and explanatory only and are not intended to be restrictive of the invention as claimed.

DETAILED DESCRIPTION OF THE PREFERRED EMBODIMENTS OF THE INVENTION

Reference will now be made in detail to present preferred embodiments of the invention, examples of which are illustrated in the following example section.

In accordance with the invention novel compositions are provided to achieve the objects in accordance with the purposes of the invention, as embodied and fully described herein, the invention comprises compositions of the general formula I:

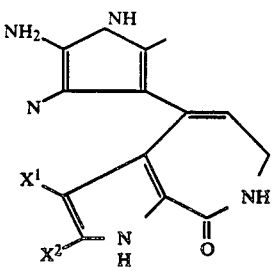

wherein $X^1$ and $X^2$ are the same or different and are a halogen, or hydrogen with the proviso that $X^1$ and $X^2$ are not both bromine.

In preferred embodiments of the invention, the composition is substantially pure and $X^1$ or $X^2$ is bromine, or hydrogen. In more preferred embodiments of the invention, the invention comprises antitumor compositions of the formulae II–V:

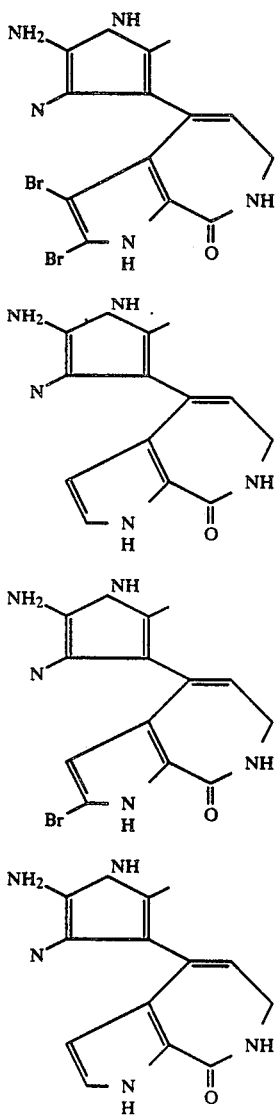

In accordance with the invention acid salt derivatives of the compositions according to formula I are also provided. These salt derivatives are formed from treatment with organic and inorganic acids. Examples of such acids include but are not limited to hydrochloric, hydrobromic, nitric, sulfuric, and acetic and trifluoroacetic acids.

In accordance with the invention, an antitumor composition is provided comprising as active ingredient an effective antitumor amount of one or more of the compositions described above and identified by formulae I–V or their acid salt derivative and a non-toxic pharmaceutically acceptable carrier or diluent. While effective amounts may vary, as conditions in which the antitumor compositions are used vary, a minimal dosage required for activity is generally between 0.01 and 100 micrograms against $10^5$ tumor cells. Useful examples of non-toxic pharmaceutically acceptable carriers or diluents include, but are not limited to, the following: ethanol, dimethyl sulfoxide and glycerol.

In accordance with the invention, a method for inhibiting tumors in a host is provided comprising contacting a tumor with an antitumor amount of one or more compositions according to formulae I–V or their acid salt derivative. The effectiveness of the compositions of the invention for inhibiting tumors indicates their usefulness for controlling tumors in hosts including mammals and for treating cancerous cachexia.

In accordance with the invention, a process to produce a composition according to formulae I–V comprises the step of: collecting marine sponges *Teichaxinella morchella* and *Ptilocaulis walpersi;* contacting the sponge with a suitable organic solvent; obtaining a solvent mixture extract of the solvent; and isolating a composition according to formulae I–V.

A detailed description and explanation of a preferred embodiment of the process of the invention to produce the composition according to formula I–V is as follows: marine sponges *Teichaxinella morchella* and *Ptilocaulis walpersi* are collected from the Carribbean at various depths. The sponges are admixed with methanol or methanol-toluene (3:1) as solvent (a first solvent) in a mortar or blender. The extract is concentrated and partitioned between water (a second solvent) and chloroform (a third solvent) to give an organic aqueous phase residue. The aqueous phase is concentrated and compositions according to the invention are isolated by various chromatographic techniques from the aqueous fraction obtained.

While methanol or methanol-toluene; water and chloroform are the presently preferred choices for the first; second; and third solvents, respectively, other suitable solvents may be substituted. A suitable first solvent should be capable of extracting a compound according to any one of formulae I–V from other components of sponges. Suitable first solvents which may be substituted methanol or methanol-toluene include, but are not limited to, the following organic solvents: acetone; n-butanol; methanol; ethanol; and water. Suitable second and third solvents should be capable of extracting and separating into various fractions the various compounds of formulae I–V from other components that may be present in the first solvent extract. Suitable second and third solvents which may be substituted for either water or chloroform or both include, but are not limited to either water or chloroform alone or, the following organic solvents: methylene chloride; dichloroethane; hexane; and lower alkanes. Different ratios of first, second and third solvents and any combination may be used in the invention as would be known to those skilled in the art.

Any suitable fractionation and isolation techniques may be utilized in accordance with the process of the invention. Suitable fractionation techniques include various chromotography techniques such as, medium pressure liquid chromatography with a suitable column as would be known to those skilled in the art (e.g., Vydac C-18 protein and peptide stationary phase eluted with a suitable solvent such as, for example, 10% acetonitrile-90% water-0.1% TFA).

It is therefore apparent that the compositions of the invention, the processes for producing the compositions of the invention and the methods for utilizing the compositions of the invention to inhibit tumors are effective for inhibiting or destroying tumors and therefore controlling diseases caused by or related to such tumors in fulfillment of the objects of the invention.

EXAMPLES

The invention will now be illustrated by examples. The examples are not intended to be limiting of the scope of the present invention. In conjunction with the detailed and general description above, the examples provide further understanding of the present invention and outline a process for producing compositions of the invention.

The following examples represent preferred embodiments of the compositions, processes and methods of the invention for satisfying the stated objects of the invention. The starting materials and reagents in the examples whose method of preparation are not indicated are commercially available from sources known to the art such as chemical supply houses.

EXAMPLE 1

Preparation of II

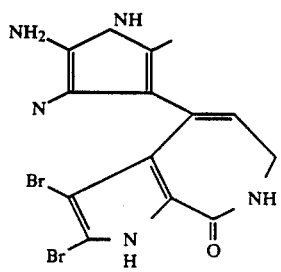

Marine sponges *Teichaxienella Morchella* and/or *Ptilocaulis walpersi* were collected from a variety of depths in the Caribbean. Twenty-five grams of the frozen sponge was admixed with 250 milliliters of methanol or methanol-toluene (3:1). The extract was filtered, and then concentrated by distillation under reduced pressure to yield 2.4 grams of residue. The residue was partitioned between water and chloroform. The aqueous phase was concentrated and chromatographed under medium pressure conditions on VYDAC C-18 protein and peptide reverse phase stationary phase with 10% acetonitrile-90% water-0.1% trifluroacetic acid as the eluent to yield 70 mg of pure II.

Spectral data for II: MS: $M+H^+C_{11}H_{10}N_5OBr_2 m/z=385.9347$ (observed), 385.9252 (calculated).

UV: $\lambda_{max}=207$ (7000); 235 (7080) in methanol.

Proton NMR: d4-methanol 250 MHz; 3.57 (d J=7.2 Hz, 2H); 6.26 (t J=7.2 Hz, 2H); 6.80 (s 1H). d6-DMSO 400 MHz: 3.44 (t J=4.8, 2H); 6.20 (t J=6.8); 6.88 (s); 7.42 (s); 8.11 (t J=5.2, 2H); 12.1 (s); 12.3 (s); 13.3 (s).

Carbon NMR: d4-methanol 400 MHZ; 167.3 s; 148.9 s; 129.1 s; 127.6 s; 126.9 d; 126.7 s; 123.4 s; 112.7 d; 109.7 s; 99.4s; 38.8 t.

EXAMPLE 2

Preparation of III

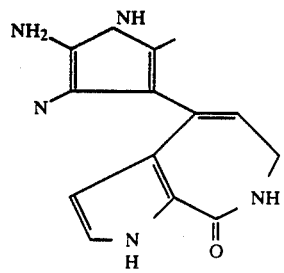

III is prepared by catalytic hydrogenation of the tetrasilyl derivative formed by treatment of II with hexamethyldisilazane in tetrahydrofuran/dioxane. Aqueous or acidic workup cleaves the silyl protecting groups yielding III.

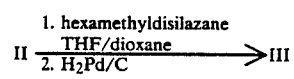

EXAMPLES 3 and 4

Preparation of IV and V

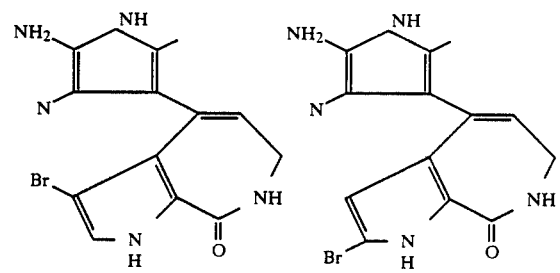

A mixture of IV and V is separated by chromatographic means and is prepared by treatment of the tetrasilyl derivative of II prepared by treatment of II with hexamethyldisilazane in tetrahydrofuran/dioxane with an active metal such as Mg, or Zn. Aqueous or acidic work up cleaves the protecting groups yielding a mixture of IV and V which would be separated by chromographic means.

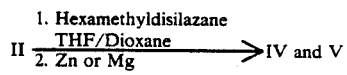

EXAMPLE 5

Preparation of acid salts

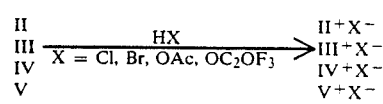

ANTITUMOR ACTIVITIES OF THE COMPOUNDS OF THE INVENTION

The following assay method was utilized to illustrate the antitumor effectiveness of the compositions of Formula II corresponding to the product of example 1.

L1210 MOUSE LEUKEMIA CELL ASSAY

Maintenance of Cell Line

L1210 mouse leukemia cells are grown in Dulbecco MEM medium with 10% horse serum, 4 mM glutamine, and 20 ug/ml gentamycin (Biologos, Inc.). Cells are incubated in 10% $CO_2$ and subcultured 2 times per week.

PROCEDURE

1. Add compound to each well of a 24-well plate or tube and allow solvent to evaporate to dryness.
2. Add 2 ml ($1.2 \times 10^5$) cells to each well or tube and mix.
3. Incubate in 10% $CO_2$ at 37° for 48 hours.
4. Read plates with an inverted microscope, scoring activity from ND to 4+ as follows: ND (not detectable), >90% of negative control growth; 1+, 75–90 % of negative control growth; 2+, 50–74% of negative control growth; 3+, 25–49% of negative control growth; 4+ <25% of negative control growth. Cell counts are performed on each tube and results are reported as percent of control. The negative control is solvent only. The positive control is vinblastine or vincristine in aqueous solution at final concentrations of 0.001, 0.01, 0.1 and 1.0 ug/ml.

Composition of formula II is cytotoxic in vitro against L-1210 murine leukemia cells, with an $IC_{50}$ of approximately 10 ug/ml. Such demonstrated in vitro activity is indicative of the effectiveness of the compositions of the invention as antitumor agents.

The scope of the present invention is not limited by the description, examples, and suggested uses herein and modifications can be made without departing from the spirit of the invention. For example, it may be noted that other derivatives of the composition of example 1 such as a fluorinated derivative may possess antitumor activity analogous to those preferred embodiments described above. Further, the compositions described herein may have other useful applications such as, for example, analgesic applications. Application of the compositions of the present invention can be accomplished by any suitable therapeutic method and technique as is presently or prospectively known to those skilled in the art. Thus, it is intended that the present invention cover the modifications and variations of this invention provided that they come within the scope of the appended claims and their equivalents.

What is claimed is:

1. A compound according to the formula:

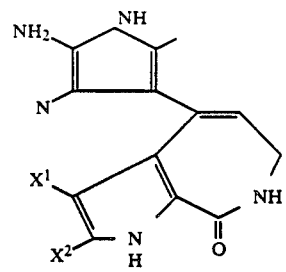

wherein $X^1$ and $X^2$ are the same or different and are a halogen or hydrogen with the proviso and that $X^1$ and $X^2$ are not both bromine.

2. A compound according to claim 1 wherein at least one of $X^1$ and $X^2$ are Br or H.

3. A compound according to claim 1 selected from the group consisting of:

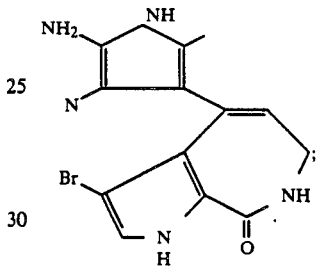

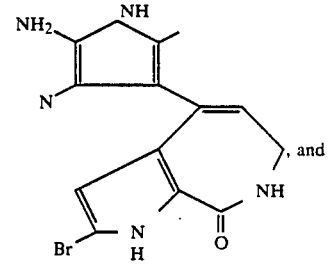

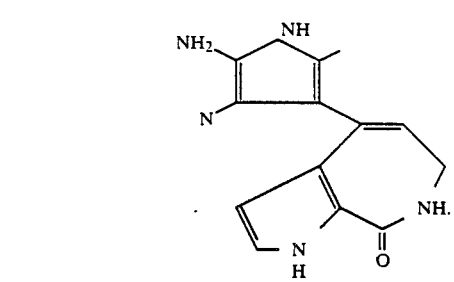

4. The compound according to claim 1 wherein said composition is substantially pure.

5. An acid salt derivative of a compound according to claim 1 wherein the acid salt derivative is a salt of an acid selected from the group consisting of hydrochloric, hydrobromic, nitric, sulfuric, acetic and trifluoroacetic acid.

6. An antiumor composition comprising, a active ingredient, an effective antitumor amount of one or more of the compounds of claim 1 and a non-toxic pharmaceutically acceptable carrier or diluent.

7. An antiumor composition comprising, as active ingredient, an effective antitumor amount of one or more of the compounds of claim 3 and a non-toxic pharamceutically acceptable carrier or diluent.

8. A method for inhibiting tumors in a host comprising contacting a tumor with an effective amount of a compound according to the formula:

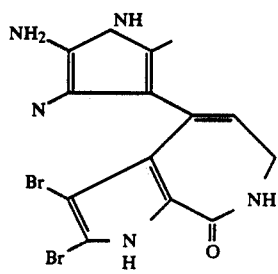

9. A method for inhibiting tumors in a host comprising contacting a tumor with an effective antitumor amount of one or more compounds of claim 1.

10. A method for inhibiting tumors in a host comprising contacting a tumor with an effective antitumor amount of one or more compounds of claim 3.

11. A method for inhibiting tumors in a mammalian host comprising contacting a tumor with an effective antitumor amount of one or more compounds of claim 1.

12. A method for inhibiting tumors in a mammalian host comprising contacting a tumor with a effective antitumor amount of one or more compounds of claim 3.

13. The method according to claim 8 wherein the host is a mammalian host.

14. A process to produce a compound according to claim 1 comprising the steps of:

collecting marine sponges *Teichaxinella morchella* and *Ptilocaulis walperi;* contacting said sponges with a suitable organic solvent;

obtaining an extract of the sponge and sovent mixture; and obtaining a compound according to claim 1 from the extract.

15. A process according to claim 14 wherein the compound is subjected to hydrogenation before the compound is obtained.

16. A process to produce a compound according to claim 8 comprising the steps of:

collecting marine sponges *Teichaxinella morchella* and *Ptilocaulis walpersi;* contacting said sponges with a suitable organic solvent;

obtaining an extract of the sponge and solvent mixture; and obtaining a compound according to claim 8 from the extract.

17. A process according to claim 14 wherein an acid salt derivative is formed by treatment of the compound with an inorganic or organic acid.

18. A therapeutic method for treating cancerous cachexia caused by the presence of a tumor in a host comprising contacting cells of said tumor with an effective antitumor amount of a compound according to claim 1.

19. A therapeutic method for treating cancerous cachexia caused by the presence of a tumor in a host comprising contacting cells of said tumor with an effective antitumor amount of a compound according to claim 3.

20. A therapeutic method for treating cancerous cachexia caused by the presence of a tumor in a host comprising contacting cells of said tumor with an effective antitumor amount of a compound according to claim 8.

* * * * *